United States Patent [19]

Bimond et al.

[11] 4,210,025

[45] Jul. 1, 1980

[54] PNEUMATIC COMPENSATOR FOR A FLUID SAMPLING CELL

[75] Inventors: Jean-Pierre Bimond; Flavien Lazarre, both of Pau; André Puyau, Lescar, all of France

[73] Assignee: Societe Nationale Elf Aquitaine (Production), Paris, France

[21] Appl. No.: 662

[22] Filed: Jan. 3, 1979

[30] Foreign Application Priority Data

Jan. 4, 1978 [FR] France .............................. 78 00122

[51] Int. Cl.² .............................................. G01N 1/12
[52] U.S. Cl. .................................. 73/421 R; 73/155; 73/425.4 R
[58] Field of Search ............. 73/421 R, 422 R, 421 B, 73/155

[56] References Cited

U.S. PATENT DOCUMENTS

| | | | |
|---|---|---|---|
| 3,203,247 | 8/1965 | Bicek | 73/421 R |
| 3,323,361 | 6/1967 | Lebourg | 73/155 |
| 3,859,850 | 1/1975 | Whitten et al. | 73/155 |

Primary Examiner—S. Clement Swisher
Attorney, Agent, or Firm—Brisebois & Kruger

[57] ABSTRACT

An apparatus and a process for handling samples of fluids under pressure to maintain the fluid in a monophasic state.

In said apparatus and process the pressure variations of said fluid sample are limited so as to maintain the same in the monophasic state, by varying the volume available for said fluid sample in accordance with any variations of the temperature of the same.

6 Claims, 5 Drawing Figures

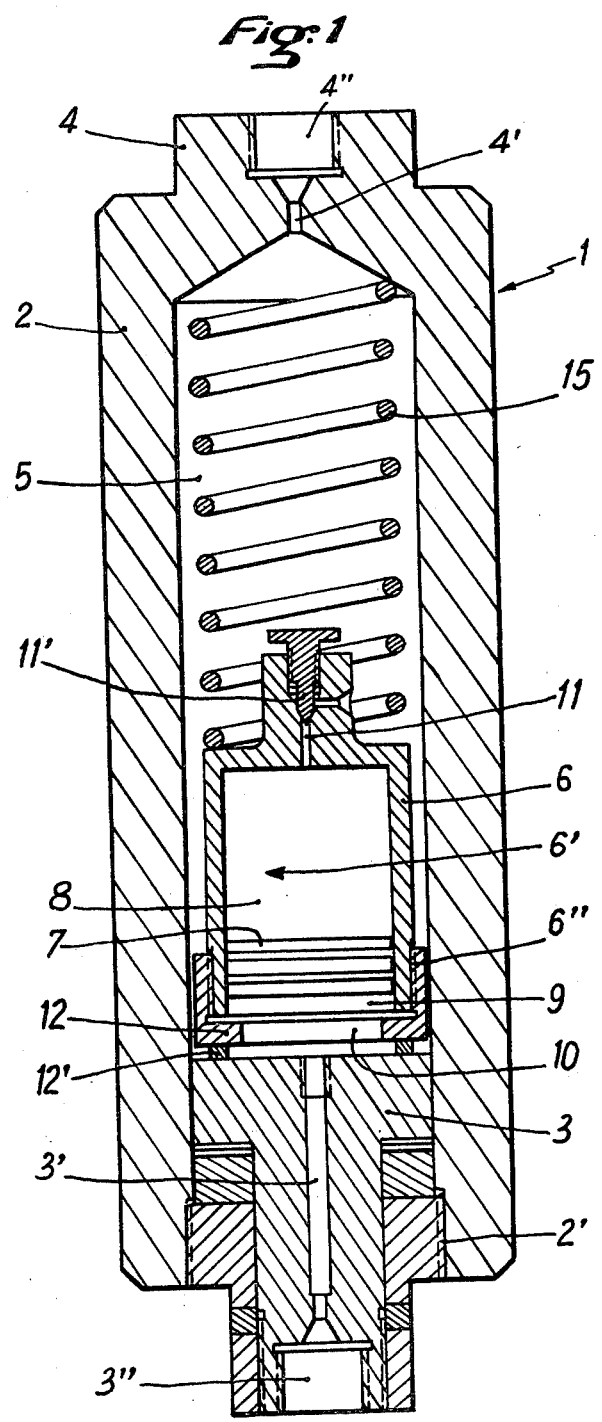

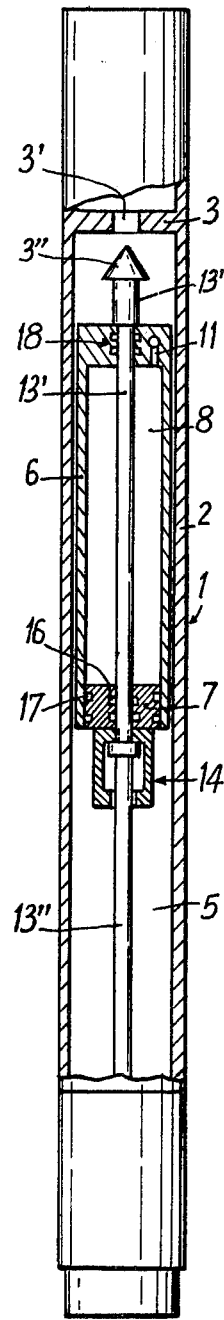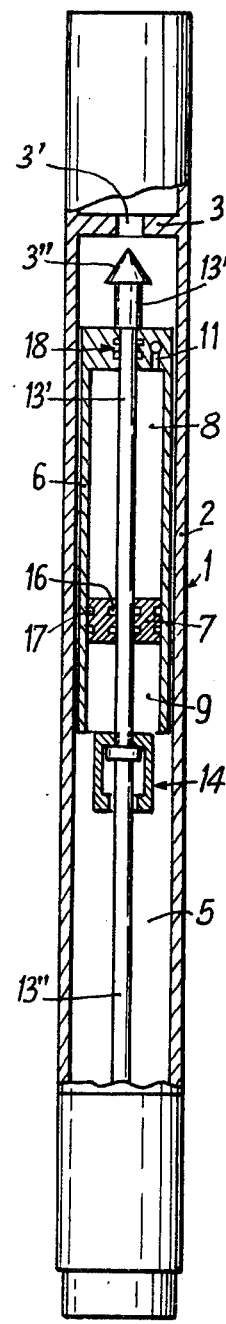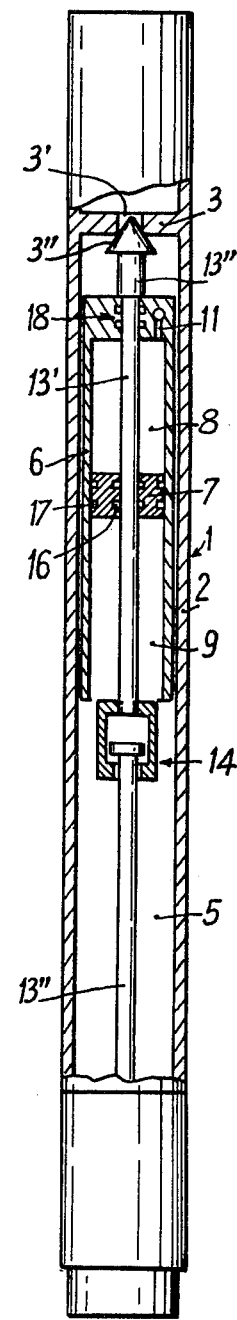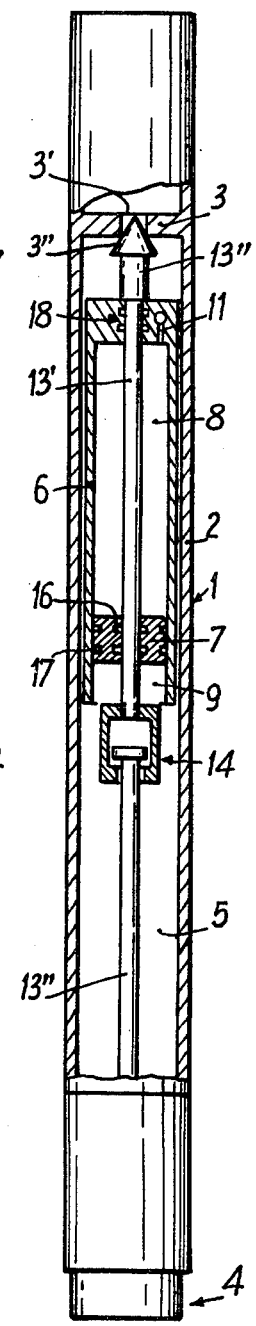

PNEUMATIC COMPENSATOR FOR A FLUID SAMPLING CELL

The present invention is related to a process for handling samples of fluids under pressure to maintain the fluid in a monophasic state.

Various types of cells are already known for the sampling of fluids in conditions of temperature and pressure such as, for example, those encountered in hydrocarbon deposits. These cells are used for raising the sample to the surface and carrying it to the laboratory. Certain types of cells are specially designed for carrying samples.

In various types of cells, the decrease in temperature during the raising of the sample results in a reduced pressure which may in many cases bring the fluid to temperature and pressure conditions corresponding to the dew point or to the bubble pressure.

In general, when the cell arrives at the laboratory, it is entered into an oven where its temperature is raised to that of the deposit with a view to causing the sample to resume its initial monophasic state. This result is obtained all the more efficiently when the fluid has a low heavy component content. However, when the fluid contains asphaltenes and paraffins in a colloidal dispersion state, and when these products have been segregated it is no longer possible to reintegrate them into the fluid. In such a case the properties of the fluid on which the thermodynamic measures are made in the laboratory do no more exactly correspond to those of the fluid in the deposit.

An object of the present invention is to overcome this difficulty by means of a handling process which allows the fluid to be maintained in a monophasic state.

According to the invention, in the process of handling fluids under pressure, in order to maintain a fluid in a monophasic state, the pressure variations of this fluid, when the temperature of the sample varies, are limited by varying the volume afforded for this fluid sample in the same way as the temperature variations.

In such a process the volume afforded for a sample is varied by making said volume complementary to an auxiliary volume containing a gas of the group of gases whose critical temperature is lower than the lowest temperature possible during handling and the value of the auxiliary volume occupied by said gas under given temperature and pressure conditions is determined in such a way that, afterwards, a temperature variation results in a volume variation of the sample, correlative to a variation of the volume of the auxiliary gas, such that the sample pressure remains higher than the bubble or dew pressure of said sample.

A device according to the invention, for limiting during handling the pressure of a fluid sample which occupies a volume in a space within a cell, comprises an enclosure having an auxiliary volume which varies between a zero and a maximum value, said auxiliary volume being located in the inner space of the cell, and being complementary to the volume occupied by the fluid sample, said auxiliary volume containing a gas under pressure selected in the group of gases whose critical temperature is lower than the lowest temperature possible during handling, the value of the auxiliary volume occupied by said gas under given temperature and pressure conditions being determined in such a way that, for various temperature values, the sample pressure is always higher than the bubble or dew presure of said sample.

According to a preferred embodiment of the invention, the variable volume enclosure is constituted by a cylinder within which a piston is displaceable by a translational motion and sealingly engaging the cylindrical wall of the enclosure said cylinder being provided with communication means, which can be obturated or disconnected with respect to a gas feeding means under a predetermined pressure.

Such a device is generally provided with means for setting the enclosure in a stable position within the inner space of the cell, said means being preferably elastic.

In the various embodiments, in order to make it easier to detect possible leaks, the gas under pressure is a tracer which is not present in the samples likely to be stored in the cell, for instance carbon tetrafluoride.

The invention will be better understood in the following no limitative description of devices with which it is possible to carry out the process of the invention, illustrated by the following figures in which:

FIG. 1 is a pneumatic compensator fitted in a fluid handling cell.

FIGS. 2, 3, 4, 5 show a pneumatic compensator fitted in a fluid sampling cell having self-closing valves.

FIG. 2 is a pneumatic compensator, filled in a sampling cell having self-closing valves, after the surface filling.

FIG. 3 is a cell according to FIG. 2 during lowering in a well.

FIG. 4 is a cell according to FIG. 2 after closing.

FIG. 5 is a cell according to FIG. 2 after raising to the surface.

FIG. 1 is a diagram of a pneumatic compensator fitted in a inlet sampling cell or in a cell for carrying fluid on the surface.

Such a cell 1 is constituted by a hollow cylindrical sheath 2 both ends of which are obturated by end-pieces at least one of which is a cap 3 and the other is an end-piece 4 both of which are shown in section.

Conduits 3' and 4' go respectively through end-pieces 3 and 4, each of them being provided with a needle valve located in the recesses shown in 3" and 4".

End-piece 3 in FIG. 3 is constituted by a cap attached to sheath 2 by means of a thread 2'.

The cell 1 defines an inner space 5 in which a pneumatic compensation is located which is constituted by a metallic cylindrical enclosure 6 containing a cylindrical piston 7 which is movable translationally while sealingly engaging the cylindrical inner wall 6' of said metallic enclosure 6.

The piston 7 defines in the cylindrical enclosure 6 two spaces 8 and 9 the sum of the volumes of which is constant.

Only one of the two spaces 8 and 9, for example space 9, communicates with the inner space 5 of the cell through an opening 10; the other space 8 is connected to the inner space 5 of the cell by conduit 11 provided with a valve 11'. Conduit 11 and valve 11' constitute the filling means of space 8.

Cylindrical enclosure 6 is provided with a removable ring 12 which defines an extra thickness and constitutes a stop limiting the translational movement of piston 7 towards opening 10.

On FIG. 1, movable ring 12 defines the outline of opening 10; it is removably attached to wall 6' of enclosure 6 by means of a thread 6". Ring 12 is provided with at least three wedges such as 12' by means of which said ring 12 rests on inner wall 3' of cap 3 while allowing the fluid which fills the inner space 5 to flow freely.

Whatever the temperature may be, the volume of space 8 on the one hand and the volume remaining available in the inner space 5 of the cell for the fluid sample, on the other hand, are complementary, their sum being constant.

The pneumatic compensator shown in FIG. 1 is blocked in the inner space 5 of cell 1 by means of a spring 15 resting on the one hand on the pneumatic compensator and on the other hand on the inner profile of end-piece 4 of cell 1.

The volume $V_1$ of space 8 at a temperature $T_1$ is so calcualted that when the temperature of the cell is brought to a valve $T_2$ lower than $T_1$, the volume increase of space 8 then compensating an equivalent reduction of the volume occupied by the sample, said volume increase is sufficient for causing the sample pressure to be such that said sample remains monophasic.

With a cell fitted with such a device, it is possible to take a sample of monophasic fluid at a pressure $P_1$ and at temperature $T_1$ and then to bring the cell and its content to a temperature $T_2$ lower than $T_1$, the sample remaining monophasic.

FIGS. 2, 3, 4 and 5 each show the diagram of the same pneumatic compensator fitted in a fluid sampling cell having self-closing valves of the fluid circulation type.

Such a cell 1 is composed of a hollow cylindrical sheath 2 both ends of which are closed by end-pieces such as end-piece 3, shown in section, and opposite to 3 an end-piece 4, not shown on the diagram. A conduit 3', coaxial to sheath 2, extends through ech of the two end-pieces such as 3, the inner opening of said conduit being used as a resting area for a closing means such as a needle 3'', shown in section, and a needle 4'', not shown on the diagrams.

The opposite needles 3'' and 4'' are respectively attached to the ends of two rod elements 13' and 13'', said rod elements being interconnected by a slide 14 of a type known per se.

A pneumatic compensator is attached to rod element 13'. Said pneumatic compensator comprises a cylindrical metallic enclosure 6 coaxial to said rod element 13''; this cylindrical enclosure 6 is closed at one end by an annular piece 15 sealingly resting, through a central opening 15', on rod element 13', while cylindrical enclosure 6 has an opening 10 at its other end.

Inside the cylindrical enclosure 6, a cylindrical piston 7 is movable in a longitudinal translational manner and sealingly engages the one hand, the cylindrical inner wall 6' of metallic enclosure 6 and, on the other hand, the smooth periphery of the rod element 13'.

On rod element 13', substantially in register with opening 10, a piece having the form of an abutment 12 integral with the rod element 13' is fitted. In the present embodiment said abutment is constituted by an element of slide 14 integral with rod element 13'. Abutment 12 restrains the movement of piston 7 inside the cylindrical sheath 6.

As shown in the diagram of FIG. 1, piston 7 defines within the cylindrical enclosure 6 two volumes 8 and 9. The cylindrical enclosure 6 is provided with a conduit 11 and a valve 11', not shown, constituting the means for filling space 8.

Whatever the temperature may be the volume of space 8 and the volume available in the cell for the fluid sample are complementary, their sum being constant.

Volume $V_1$ of the space 8 at the temperature $T_1$ is so calculated that when the cell temperature is brought to temperature $T_2$ lower than $T_1$, the volume increase of space 8 compensating an equivalent reduction of the volume occupied by the sample, said volume increase is sufficient for the sample pressure to be such that said sample remains monophasic.

A sampler having self-closing valves such as the one shown on FIG. 2 requires an inner pressure always higher than the ambiant pressure in order to ensure the lightness of the valves. For certain wells and certain sampling levels, the sampler with self-closing valves must open during the raising as the inner pressure becomes, at the top of the well, lower than the measured well top pressure. The validity significance of the samples collected under such conditions is very questionable.

The state equation of a gas is as follows:

$$W \cdot P \cdot V = Z \cdot n \cdot R \cdot T,$$

wherein:
W is the molecular weight,
P = the pressure,
V = the volume,
Z = the compressibility factor or deviation from the law of perfect gases,
n = the weight,
R = the constant of perfect gases, and
T = the absolute temperature.

For a well where, at the bottom, at 160° C., P=510 bars, at the surface, at 20° C., P=350 bars and where, the isotherms of the factor Z of the gas sample being known, Z bottom=1.157 and Z surface=0.67, the following equation results:

$$\frac{(PV) \text{ at } 20° \text{ C.}}{(PV) \text{ at } 160° \text{ C.}} = \frac{(Zn\ RT) \text{ at } 20° \text{ C.}}{(Zn\ RT) \text{ at } 160° \text{ C.}}$$

and consequently: $\left(\frac{Z}{P}\right)$ at 20° C. $= \frac{1.157 \cdot 433}{510 \cdot 293} = 3.352 \times 10^{-3}$ corresponding at the top of the well, to a sample pressure of about 200 bars, lower by 150 bars than the surface pressure.

Under such sampling conditions, the use of an hydraulic compensator results in maintaining in the cell a pressure high enough to keep the fluid sample monophasic, this pressure being moreover always higher than the ambient pressure, which ensures that the valves remain permanently closed.

Each of FIGS. 2, 3, 4 and 5 shows the relative position of the various elements described above, which constitute a sampling cell with self-closing valves of the circulation type, and a pneumatic compensator located in the cell.

FIG. 2 shows the sampling cell at the surface after the compensator has been fitted with the amount of gas required for the contemplated use.

Slide 14 is in a retracted position, wherely needles 3'' and 4'' are disengaged from their respective seats and clear the passages of conduits 3' and 4'.

The inner volume of the pneumatic compensator then reaches its maximum valve, while enclosure 6 engages annular stop 13'' integral with rod 13' and located close to needle 3″, the piston 7 engaging the body of slide 14. Piston 7 is in contact with the rod 13′ through sealing means 16 and with the inner surface of the cylindrical enclosure 6 through sealing means 17.

FIG. 3 shows the same cell when being lowered in a well, for instance a production oil well.

Slide 14 is always in a retracted position, so that conduits 3′ and 4′ remain open, which is necessary in the case of a sampling cell of the circulation type.

The inner volume of the pneumatic compensator is smaller than it is on FIG. 2. Enclosure 6 still engages annular stop 13″ which is integral with rod 13′ and located close to the needle 3′, although this is not an absolute requirement since the enclosure is slidably fitted on the rod 13′, the annular contact area between the body of enclosure 6 and rod 13′ being provided with sealing means such as 18′.

FIG. 4 shows the same cell after the collection of the fluid sample by circulation. The closing of the end openings is initiated either by surface control or by the release of a closing mechanism controlled by a timing or clock device, or by any other convenient means.

Slide 14 is in a fully extended position so that conduits 3′ and 4′ are closed by the corresponding needles 3″ and 4″.

The volume of space 8 of the pneumatic compensator is reduced as compared to the condition shown in FIG. 3, due to the displacement of the annular piston 7 provided in cylindrical enclosure 6.

When a fluid sample is being collected in a well, the volume of space 8 of the compensator corresponds to the valve at which the gas volume in the compensator is in balance with the natural fluid under the given temperature and pressure conditions prevailing at the sampling location.

FIG. 5 shows the same cell after it has been raised to the surface.

The conduits 3′ and 4′ are still closed by the corresponding needles 3″ and 4″ rince the pressure within the cell, due to the pneumatic compensator, is always maintained at a level higher than that of the external pressure.

The volume of space 8 of the compensator is so selected that the gas volume in the compensator balances the fluid contained in the cell under the temperature and pressure conditions prevailing when said cell reaches the surface, when being removed from the well.

The temperature at the surface is lower than the temperature at the bottom where the sampling has been carried out. The volume afforded for the fluid will have diminished during the raising of the cell so as to maintain the pressure at a level higher than that of the bubble or dew pressure; correlatively, the volume of space 8 of the pneumatic compensator will have increased, as the invention consists in the fact that the two volumes are associated by a device which makes them mutually complementary.

The problem to be solved is that of the assessment under given temperature and pressure conditions of the gas volume which has to be introduced intro space 8 of the compensator in order that a sample taken under certain temperature and pressure conditions may remain in the monophasic state when it is subjected to handling operations during which the temperature varies and, particularly, in the case of handling operations resulting in transferring the sample from bottom to surface conditions.

This problem has been solved by calculating the thermodynamic balances. For increased safety it is possible, in a simplified calculation, not to take into account the solid volume of the compensator.

On the basis of the following definitions:

V = cell capacity or cell net inner volume, without compensator
$h_f$ = volume mass of the oil under depth conditions
$h_s$ = volume mass of the oil under surface conditions
$g_f$ = volume mass of the gas under depth conditions
$g_s$ = volume mass of the gas under surface conditions
H = volume of the sample in the cell
G = volume of the gas in the compensator, and knowing the volumes and the volume masses, it is possible to calculate the product masses, which remain constant whatever the pressure and the temperature (sample mass = H·h and gas mass = G·g).

As: $H_f = H_s (h_s/h_f)$, hence $$\Delta H = H_f - H_S = H_s \left( \frac{h_s}{h_f} - 1 \right)$$

And also:

$$G_f = G_s \frac{g_s}{g_f}$$

$$\Delta G = G_s - G_f = G_s \left( 1 - \frac{g_s}{g_f} \right)$$

$\Delta G$ and $\Delta H$ being equal in absolute value and as $H_s$ is equal to $(V - G_s)$ $$H_S \left( \frac{h_s}{h_f} - 1 \right) = G_s \left( 1 - \frac{g_s}{g_f} \right) = (V - G_s) \left( \frac{h_s}{h_f} - 1 \right)$$

$$\frac{G_s}{V} = \frac{\frac{h_s}{h_f} - 1}{\frac{h_s}{h_f} - \frac{g_s}{g_f}}$$

$h_f$ and $h_s$ are given and therefore the gas has to be selected in such a manner that $g_s/g_f$ be lower than 1 in order that $G_s$ be lower than V, whereby the manufacture of the apparatus becomes feasible.

The invention is illustrated by, without being confined to, the following example.

EXAMPLE 1

In this example the calculations are made using the Katz and Standing charts as represented on Pages 476 and 477 of the "Handbook of Natural Gas Engineering", published by Mac Graw Hill Book Company Incorporated, New-York-Toronto-London, 1959 issue.

Nevertheless, in order to facilitate the reading to this document, some of the values indicated in decimal, or metric, units have been converted into values as commonly expressed in English-speaking countries, appearing in brackets.

The units most frequently used hereafter are:
one cubic foot (cu.ft) . . . = 28.317 cubic decimeters
one pounds (lb) . . . = 453.592 gramms
one barrel (bbl) . . . = 158.9 cubic decimeters
one degree A.P.I. (Petroleum Engineer's Association) for the density at 15° C. . . . = 141.5/(degrees A.P.I. + 131.5)
the pound per square inch (PSI) . . . = 0.068948 bar.

Data:

An oil-field has the following depth characteristics:
Pressure (P) . . .
 = 168 bars (2469.6 PSI)
Temperature (T) . . .
 = 89° C. (102° F.)
Ratio of the volume, in liters, of gas set free when the sample
 is brought to 1 bar (14.70 PSI)
 and 15° C. (590° F.), to the volume of the degassed oil obtained under the same conditions . . .
 = 710 cubic feet per barrel
This ratio is the so called GOR, i.e. Gas-Oil-Ratio.
Density, as compared to water, of the degassed oil, or storage oil . . .
 = 0.816 (42° API)
Density of the gas as compared to air . . .
 = 0.917.

Calculation:

With the help of the Katz and Standing chart n. 3, page 477 of the above mentioned Handbook, the saturation pressure is first determined, for two extreme temperatures.

89° C. (192° F.) = saturation pressure: 156 bars (2293.3 PSI)

150° C. (59° F.) = saturation pressure: 109 bars (1602.3 PSI)

In order to avoid degassing, a safety margin of 11 bars (16.17 PSI) is deemed necessary; at 15° C. (59° F.) the minimum pressure will be 120 bars (1764 PSI).

The Katz and Standing charts, page 477, enable to calculate the values $h_s$ and $h_f$ from the above-mentioned specifications relating to oil in oil fields.

At a temperature of 15.56° C. (60° F.) the "liquid" volume mass of the gas dissolved in the oil may first be estimated at bar (14.7 PSI).

The result is 0.421 g/cm$^3$ (26.3 lb/cu.ft).

Starting from 1 barrel of storage oil, 710 cu.ft of gas are to be added, i.e. $71 \times 0.917 \times 0.0755 = 49.16$ lb of gas, or in volume 1.87 cu.ft of dissolved gas (0.755 is the air volume mass at 60° F. and 14.7 psia expressed in lb/cu.ft).

As 1 barrel equals 5-615 cu.ft, the total volume of recombined fluid (storage oil a dissolved gas) yielding 1 barrel of storage oil is:

$5.615 + 1.87 = 7.485$ cu.ft at 60° F. and 14.7 psia.

The mass of this amount of gassed oil or recombined fluid is: 49.16 lb gas + 1 bbl × 0.816 × 5.615 cu.ft/bbl × 62.4 lb/cu.ft = 335.07 lb
(knowing that the water volume mass is 62.4 lb/cu.ft at 60° C. and 14.7 psia).

Therefore the volume mass of this gassed oil is: 335.07 lb/7.485 cu.ft = 44.77 lb/cu.ft.

Using charts 24 and 25 of pages 36 and 37 respectively, of Standing's handbook, it becomes possible to estimate the volume masses of the field fluid in depth and surface conditions:

$h_f = 42.0$ lb/cu.ft
$h_s = 45.4$ lb/cu.ft.

On the other hand, the values $g_f$ and $g_s$ of the volume masses of the gas contained in the compensator can be calculated from a state equation or by means of a data chart such as the DIN charts for nitrogen and argon in "Thermodynamic Functions of Gases—F. DIN—Published by Butterworths, London 1962".

If the selected gas is nitrogen:

$g_s = 0.1418$ g/cm$^3$
$g_f = 0.1481$ g/cm$^3$

The numerical application is:

$$G_s/V = (1.0802 - 1)/(1.0802 - 0.9575) = 0.653$$

Therefore, 65.3% of the inner volume of the cell must be occupied by the gas in the compensator, under a pressure of 120 bars and at 15° C. (without taking into account the solid volume of a few cm$^3$ of the compensator).

If the cell has an inner volume of 850 cm$^3$, and the device is used at an ambient temperature of 15° C.:

$(850 \times 0.653)$ cm$^3$ nitrogen, i.e. 78.73 g
and a volume available for the sample of:
$850 (1 - 0.653) = 294.8$ cm$^3$, at 15° C.

The following can then be calculated:

$$\frac{G_f}{V} = \frac{\frac{h_f}{h_s} - 1}{\frac{h_f}{h_s} - \frac{g_f}{g_s}}$$

which, for the same values of h and g, gives:

$G_f/V = 0.626$ and thus leaves space for the oil under depth conditions at a volume of 37.4% of the cell capacity.

If the cell has an inner volume of 1200 cm$^3$ (without compensator), the oil volume in depth conditions will be:

$1250 \times 0.374 = 467.5$ cm$^3$ at 168 bars and 89° C.

The above calculation provides the essential elements for the selecting of the compensator and the gas most suitable under given sampling or handling conditions.

Naturally, this invention is in no way confined to the Example and embodiments described above; many variant forms are possible for someone skilled in the art, depending on applications, and without any departure from the spirit of the invention.

What is claimed is:

1. A device for limiting during handling the pressure of a fluid sample occupying a volume in a space within a cell, comprising an enclosure with an auxiliary volume, variable between a zero volume and a maximum volume, located in the inner space of the cell, said auxiliary volume being complementary to the volume occupied by the fluid sample, said auxiliary volume containing a gas under pressure, selected from the group of the gases the critical temperature of which is lower than the lowest possible temperature likely to occur during the handling, the value of the auxiliary volume, occupied by said gas under given temperature and pressure conditions, being selected in such a way that, for various temperature values, the sample pressure is always higher than the bubble or dew pressure of said sample, and the gas under pressure is a tracer gas which is not present in the samples likely to be stored in the cell.

2. A device according to claim 1, wherein the gas under pressure is carbon tetrafluoride.

3. A process for obtaining and handling samples of at least one fluid under pressure, wherein the pressure variations of said fluid sample are limited so as to maintain the same in the monophasic state, by varying the volume available for said fluid sample in accordance with any variations of the temperature of the same, comprising the steps of:

providing a sample chamber, providing wholly within the sample chamber, a variable volume compensating unit defining an auxiliary volume and having a gas filling opening within the sample chamber and devoid of any communication with the space outside the chamber, filling into the compensating unit through the gas fill opening to a predetermined pressure a gas selected from the group of gases the critical temperature of which is lower than the lowest temperature likely to occur during handling, sealing said filling opening, introducing a fluid sample into the sample chamber after sealing the filling opening, and sealing the sample chamber after introduction of the fluid sample, said steps of providing said compensating unit and filling it with gas including selecting a compensating unit such that the auxiliary volume occupied by said gas under given temperature and pressure conditions and any subsequent modification of the temperature results in a modification of the sample volume related to variations of the auxiliary gas volume, in such a way that the sample pressure remains higher than the bubble or dew pressure of said sample.

4. A device for limiting during handling the pressure of a fluid sample occupying a volume in a space within a cell, comprising an enclosure with an auxiliary volume, variable between a zero volume and a maximum volume, located in the inner space of the cell, said auxiliary volume being complementary to the volume occupied by the fluid sample, said auxiliary volume containing a gas under pressure, selected from the group of the gases the critical temperature of which is lower than the lowest possible temperature likely to occur during the handling, the value of the auxiliary volume, occupied by said gas under given temperature and pressure conditions, being selected in such a way that, for various temperature values, the sample pressure is always higher than the bubble or dew pressure of said sample, and wherein said enclosure of variable volume is constituted by a cylinder in which a piston is translationally movable, and sealingly engaging the cylindrical wall of the enclosure, said cylinder being provided with sealable means contained wholly within the cell for feeding a gas under a predetermined pressure into said cylinder, and means for sealing said cell to isolate a space within the cell containing the fluid sample volume and the cylinder and its gas fill means.

5. A device according to claim 4, provided with means for locking the enclosure in a stable position in the inner space of the cell.

6. A device according to claim 4, provided with elastic means for mounting the enclosure in a stable position in the inner space of the cell.

* * * * *